(12) United States Patent
Khandaker et al.

(10) Patent No.: US 10,953,133 B2
(45) Date of Patent: Mar. 23, 2021

(54) PROCESS TO CREATE 3D TISSUE SCAFFOLD USING ELECTROSPUN NANOFIBER MATRIX AND PHOTOSENSITIVE HYDROGEL

(71) Applicant: UNIVERSITY OF CENTRAL OKLAHOMA, Edmond, OK (US)

(72) Inventors: Morshed Khandaker, Edmond, OK (US); Shahram Riahinezhad, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 104 days.

(21) Appl. No.: 15/439,650

(22) Filed: Feb. 22, 2017

(65) Prior Publication Data

US 2017/0239388 A1    Aug. 24, 2017

Related U.S. Application Data

(60) Provisional application No. 62/298,627, filed on Feb. 23, 2016.

(51) Int. Cl.

| | | |
|---|---|---|
| *A61L 27/26* | (2006.01) | |
| *D04H 1/728* | (2012.01) | |
| *A61L 27/48* | (2006.01) | |
| *B29C 64/165* | (2017.01) | |
| *B33Y 10/00* | (2015.01) | |
| *B33Y 70/00* | (2020.01) | |
| *B33Y 80/00* | (2015.01) | |
| *A61L 27/38* | (2006.01) | |
| *A61L 27/52* | (2006.01) | |
| *A61L 27/54* | (2006.01) | |
| *A61L 27/56* | (2006.01) | |
| *C12N 5/00* | (2006.01) | |
| *C12N 5/04* | (2006.01) | |
| *C12N 5/071* | (2010.01) | |
| *C12N 5/077* | (2010.01) | |
| *D01D 5/00* | (2006.01) | |
| *D06M 15/27* | (2006.01) | |
| *D06M 23/14* | (2006.01) | |
| *D01F 6/62* | (2006.01) | |
| *B29K 105/00* | (2006.01) | |
| *B29L 31/00* | (2006.01) | |
| *D06M 101/32* | (2006.01) | |

(52) U.S. Cl.
CPC .......... *A61L 27/26* (2013.01); *A61L 27/3804* (2013.01); *A61L 27/3813* (2013.01); *A61L 27/3817* (2013.01); *A61L 27/48* (2013.01); *A61L 27/52* (2013.01); *A61L 27/54* (2013.01); *A61L 27/56* (2013.01); *B29C 64/165* (2017.08); *B33Y 10/00* (2014.12); *B33Y 70/00* (2014.12); *B33Y 80/00* (2014.12); *C12N 5/0012* (2013.01); *C12N 5/0062* (2013.01); *C12N 5/04* (2013.01); *C12N 5/0625* (2013.01); *C12N 5/0655* (2013.01); *D01D 5/003* (2013.01); *D04H 1/728* (2013.01); *D06M 15/27* (2013.01); *D06M 23/14* (2013.01); *A61L 2300/412* (2013.01); *A61L 2400/12* (2013.01); *A61L 2430/02* (2013.01); *B29K 2105/0058* (2013.01); *B29L 2031/753* (2013.01); *C12N 2513/00* (2013.01); *C12N 2533/30* (2013.01); *C12N 2533/52* (2013.01); *C12N 2533/54* (2013.01); *D01F 6/625* (2013.01); *D06M 2101/32* (2013.01); *D10B 2509/00* (2013.01)

(58) Field of Classification Search
None
See application file for complete search history.

(56) References Cited

U.S. PATENT DOCUMENTS

| | | | |
|---|---|---|---|
| 692,631 | A | 2/1902 | Cooley |
| 1,975,504 | A | 10/1934 | Formhals |
| 2,109,333 | A | 2/1938 | Formhals |
| 2,123,992 | A | 7/1938 | Formhals |
| 2,187,306 | A | 1/1940 | Formhals |
| 2,349,950 | A | 5/1944 | Formhals |
| 5,047,055 | A | 9/1991 | Bao et al. |
| 5,674,295 | A | 10/1997 | Ray et al. |
| 6,106,913 | A | 8/2000 | Scardino et al. |
| 6,355,699 | B1 | 3/2002 | Vyakarnam et al. |

(Continued)

FOREIGN PATENT DOCUMENTS

| | | |
|---|---|---|
| CN | 1687493 A | 10/2005 |
| CN | 1766181 A | 5/2006 |

(Continued)

OTHER PUBLICATIONS

Agarwal et al., Use of electrospinning technique for biomedical applications, Polymer 49 (2008) 5603-5621.*

(Continued)

*Primary Examiner* — Sharmila G Landau
*Assistant Examiner* — Stephen M Chong
(74) *Attorney, Agent, or Firm* — Berenato & White, LLC

(57) ABSTRACT

A process providing a method to create 3D scaffolds using nano-scale fibers, comprising: deposition and alignment of a plurality of electrospun fiber layers on a substrate; application of a photosensitive biomedical polymer liquid to each fiber layer deposited on said substrate; deposition and cross-alignment of a plurality of electrospun fiber layers on said substrate; retaining said polymer liquid in place using said cross-aligned fiber layers; curing said polymer liquid on top of each fiber layer using UV light.

1 Claim, 12 Drawing Sheets

(56) References Cited

U.S. PATENT DOCUMENTS

| | | | |
|---|---|---|---|
| 6,733,533 B1 | 5/2004 | Lozier | |
| 6,743,273 B2 | 6/2004 | Chung et al. | |
| 6,746,485 B1 | 6/2004 | Zucherman et al. | |
| 6,753,454 B1 | 6/2004 | Smith et al. | |
| 6,821,479 B1 | 11/2004 | Smith et al. | |
| 6,902,932 B2 | 6/2005 | Altman et al. | |
| 6,997,956 B2 | 2/2006 | Cauthen | |
| 7,575,707 B2 | 8/2009 | Xia | |
| 7,828,539 B1 | 11/2010 | Beachley et al. | |
| 8,157,554 B2 | 4/2012 | Petras et al. | |
| 8,696,750 B2 | 4/2014 | Santerre et al. | |
| 9,044,335 B2 | 6/2015 | Bonassar et al. | |
| 9,078,731 B2 | 7/2015 | Mortarino | |
| 9,295,560 B2 | 3/2016 | Carpenter | |
| 9,359,694 B2 | 6/2016 | Khandaker et al. | |
| 2002/0104606 A1 | 8/2002 | Ohzuru et al. | |
| 2005/0090901 A1 | 4/2005 | Studer | |
| 2005/0104606 A1 | 5/2005 | Donsky | |
| 2005/0137675 A1 | 6/2005 | Dubson et al. | |
| 2005/0224998 A1 | 10/2005 | Andrady et al. | |
| 2006/0160214 A1 | 7/2006 | Masuda et al. | |
| 2006/0226580 A1 | 10/2006 | Xia et al. | |
| 2007/0269481 A1 | 11/2007 | Li et al. | |
| 2007/0275458 A1 | 11/2007 | Gouma | |
| 2008/0170982 A1 | 7/2008 | Zhang et al. | |
| 2008/0220042 A1* | 9/2008 | Hashi | A61K 38/58 514/1.1 |
| 2008/0290554 A1 | 11/2008 | Wu et al. | |
| 2009/0108503 A1 | 4/2009 | Scott-Carnell et al. | |
| 2009/0171467 A1 | 7/2009 | Mann et al. | |
| 2009/0294733 A1 | 12/2009 | Branham et al. | |
| 2009/0324950 A1 | 12/2009 | Kim | |
| 2010/0179659 A1 | 7/2010 | Li et al. | |
| 2010/0191335 A1 | 7/2010 | Root et al. | |
| 2010/0197027 A1 | 8/2010 | Zhang et al. | |
| 2010/0327494 A1 | 12/2010 | Jabbari | |
| 2011/0098826 A1 | 4/2011 | Mauck et al. | |
| 2012/0296431 A1 | 11/2012 | Kim et al. | |
| 2013/0079881 A1 | 3/2013 | Bonassar et al. | |
| 2013/0273801 A1 | 10/2013 | Young | |
| 2014/0188227 A1 | 7/2014 | Santerre et al. | |
| 2016/0047064 A1 | 2/2016 | Khandaker et al. | |
| 2016/0143745 A1 | 5/2016 | Kandel et al. | |
| 2016/0374820 A1 | 12/2016 | Khandaker et al. | |

FOREIGN PATENT DOCUMENTS

| | | | | |
|---|---|---|---|---|
| CN | 1776033 A | 5/2006 | | |
| EP | 2045375 A1 | 4/2009 | | |
| WO | WO2004074559 A1 | 9/2004 | | |
| WO | WO2005073442 A1 | 8/2005 | | |
| WO | WO2005123995 A1 | 12/2005 | | |
| WO | WO2006052039 A1 | 5/2006 | | |
| WO | WO2006135147 A1 | 12/2006 | | |
| WO | WO2009101472 A2 | 8/2009 | | |
| WO | WO 2014/176697 A1 * | 11/2014 | | B81C 1/00 |
| WO | WO2016028618 | 2/2016 | | |

OTHER PUBLICATIONS

Ali et al., "Electrospinning of Continuous Nanofiber Bundles and Twisted Nanofiber Yarns", Nanofibers—Production, Properties and Functional Applications, 2011, pp. 153-174.
Bashar Haseeb, "Controlled deposition and alignment of electrospun PMMA-g-PDMS nanofibers by novel electrospinning setups", Master of Science Thesis, KTH Chemical Science and Engineering, Stockholm, Sweden 2011, 164 pages.
KdScientific, "Inflowmation Chronicles Highlights of Interesting Scientific Applications", Inflowmation Chronicles, Issue 1001, Spring 2009, 2 pages.
Li et al., "Electrospinning of Nanofibers: Reinventing the Wheel?**", Advanced Materials, 2004, vol. 16, No. 14, pp. 1151-1170.
Monika Rajput, "Optimization of Electrospinning Parameters to Fabricate Aligned Nanofibers for Neural Tissue Engineering", A Thesis Submitted in Partial Fulfillment of the Requirement for the Degree of Master of Technology In Biotechnology & Medical Engineering, Department of Biotechnology and Medical Engineering, National Institute of Technology, Rourkela, Orissa, India, 2012, 74 pages.
Neves et al., "Patterning of polymer nanofiber meshes by electrospinning for biomedical applications", International Journal of Nanomedicine, 2007, 2(3), pp. 433-448.
Peterson, "Hybrid Nanomanufacturing Process for High-Rate Polymer Nanofiber Production", University of Nebraska—Lincoln, DigitalCommons@University of Nebraska—Lincoln, Engineering Mechanics Dissertations & Theses, 2010, 159 pages.
Tan et al., "Tensile testing of a single ultrafine polymeric fiber", Biomaterials 26, 2005, pp. 1453-1456.
Theron et al., "Electrostatic field-assisted alignment of electrospun nanofibres", Nanotechnology, 12, 2001, pp. 384-390.
Yarin et al., "Branching in electrospinning of nanofibers", Journal of Applied Physics 98, pp. 064501, 2005, pp. 1-12.
Attia et al., "The response of annulus fibrosus cell to fibronectin-coated nanofibrous polyurethane-anionic dihydroxyoligomer scaffolds", Biomaterials 32, 2011, pp. 450-460.
Bosworth et al., "State of the art composites comprising electrospun fibres coupled with hydrogels: a review", Nanomedicine: Nanotechnology, Biology, and Medicine 9, 2013, pp. 322-335.
Bowles et al., "Tissue Engineering for Regeneration and Replacement of the Intervertebral Disc", Principles of Tissue Engineering, 2014, Chapter 56, pp. 1223-1251.
Bowles et al., "Tissue-engineered intervertebral discs produce new matrix, maintain disc height, and restore biomechanical function to the rodent spine", PNAS, vol. 108, No. 32, Aug. 9, 2011, pp. 13106-13111.
Driscoll et al., "Fiber angle and aspect ratio influence the shear mechanics of oriented electrospun nanofibrous scaffolds", Journal of the Mechanical Behavior Materials 4, 2011, pp. 1627-1636.
Gloria et al., "Dynamic-mechanical properties of a novel composite intervertebral disc prosthesis", J Mater Sci: Mater Med (2007) 18, pp. 2159-2165.
Kim et al., "Notochordal cells stimulate migration of cartilage end plate chondrocytes of the intervertebral disc in in vitro cell migration assays", The Spine Journal 9, 2009, pp. 323-329.
Larraz et al., "Design and Properties of Novel Self-Curing Acrylic Formulations for Application in Intervertebral Disks Restoration", Biomacromolecules, vol. 6, No. 4, 2005, pp. 2058-2066.
Leung et al., "Tissue engineering for intervertebral disc degeneration", Orthopedic Clinics of North America, 2011, v. 42 n. 4, pp. 575-583.
Martin et al., "Translation of an engineered nanofibrous disc-like angle-ply structure for intervertebral disc replacement in a small animal model", Acta Biomaterialia 10, 2014, pp. 2473-2481.
Melrose et al., "Differential Expression of Proteoglycan Epitopes and Growth Characteristics of Intervertebral Disc Cells Grown in Alginate Bead Culture", Cells Tissues Organs, 2001, 168, pp. 137-146.
Mizuno et al., "Tissue-Engineered Composites of Anulus Fibrosus and Nucleus Pulposus for Intervertebral Disc Replacement", Spine vol. 29, No. 12, 2004, pp. 1290-1298.
Mizuno et al., "Biomechanical and biochemical characterization of composite tissue-engineered intervertebral discs", Biomaterials 27, 2006, pp. 362-370.
Nerurkar et al. "Mechanics of Oriented Electrospun Nanofibrous Scaffolds for Annulus Fibrosus Tissue Engineering", Journal of Orthopaedic Research, Aug. 2007, pp. 1018-1028.
Reitmaier et al., "Hydrogels for nucleus replacement—Facing the biomechanical challenge", Journal of the Mechanical Behavior of Biomedical Material 14, 2012, pp. 67-77.
Ruan et al., "Intervertebral disc transplantation in the treatment of degenerative spine disease: a preliminary study", www.thelancet.com, vol. 369, Mar. 24, 2007, pp. 993-999.
Silva-Correia et al., "Tissue engineering strategies applied in the regeneration of the human intervertebral disk", Biotechnology Advances 31, 2013, pp. 1514-1531.

(56) References Cited

OTHER PUBLICATIONS

Smolders et al., "Biomechanical evaluation of a novel nucleus pulposus prosthesis in canine cadaveric spines", The Veterinary Journal 192, 2012, pp. 199-205.
Vadala et al., "Bioactive electrospun scaffold for annulus fibrosus repair and regeneratioin", European Spine Journal, May 2012, 21 Suppl 1, pp. S20-S26.
Whatley et al., "Intervertebral disc (IVD): Structure, degeneration, repair and regeneration", Materials Science and Engineering C 32, 2012, pp. 61-77.
Corresponding ISR and Written Opinion dated May 22, 2017.
Theron A. et al., "Electrostatic field-assisted alignment of electrospun nanofibres", Nanotechnology 12, 2001, pp. 384-390.
Yee, W.A., et al., "Stress-induced structural changes in electrospun polyvinylidene difluoride nanofibers collected using a modified rotating disk," Polymer, 49, 2008, pp. 4196-4203.
Zussman E., et al., "Assembly of Electronspun Nanofibers into Crossbars," Nanotechnology, Aug. 27, 2002, pp. 283-286.
Jianfeng Zhang, et al., "Preparation of biaxial orientation mats from single fibers," Advances in Polymer Technol., 2010, vol. 21, pp. 606-608.
Carnell, Lisa A., et al., "Aligned Mats from Electrospun Single Fibers", Macromolecules, vol. 41, No. 14, 2008, pp. 5345-5349.
Partial EP search report for corresponding EP15833663 dated Apr. 12, 2018.

* cited by examiner

PEGDA scaffold

PCL-ENF-PEGDA scaffold

| Experimental parameters | PEGDA only | PCL-PEGDA |
|---|---|---|
| Compressive stiffness (N/mm) | 3.00± 0.12 | 5.36 ± 0.02 |
| Compressive modulus (kPa) | 259.68 ± 3.56 | 509.61± 0.006 |
| Elastic modulus (kPa) | 2.82± 0.12 | 5.34 ± 0.23 |
| Phase shift angle (degree) | 19.72± 0.40 | 5.68± 0.22 |

FIG. 9

PROCESS TO CREATE 3D TISSUE SCAFFOLD USING ELECTROSPUN NANOFIBER MATRIX AND PHOTOSENSITIVE HYDROGEL

CROSS REFERENCES TO RELATED APPLICATIONS

This application claims the benefit of U.S. Provisional Patent Application No. 62/298,627 filed on Feb. 23, 2016 in the name of Morshed Khandaker and Shahram Riahinezhad, which is expressly incorporated herein by reference in its entirety.

STATEMENT AS TO RIGHTS TO INVENTIONS MADE UNDER FEDERALLY SPONSORED RESEARCH OR DEVELOPMENT

This invention was made with government support under Grant Number 5P20GM103447 awarded by the National Institutes of Health. The government has certain rights in the invention."

FIELD OF THE INVENTION

The present invention generally relates to the field of polymer fiber production. More specifically, the invention relates to a process for the development of a thick photosensitive hydrogel scaffold by incorporating hydrogel into electrospun nanofiber membranes.

BACKGROUND OF THE INVENTION

Tissue engineering (TE) holds great promise for cultivation of patient-specific tissues for restoring organ functions and/or curing various diseases. TE techniques involve seeding or implantation of cells into scaffolds, which are biodegradable and capable of supporting three-dimensional (3D) cell growth. The need for in vitro 3D TE scaffolds that can substitute for specific tissues is becoming increasingly prevalent in TE applications ranging from fundamental scientific studies, cancer metastases, stem cell biology, drug discovery, and the replacement of organs. Current bone substitutes designed for filling bone voids caused by diseases and injuries, lack the microstructure required for successful bone growth in 3D. This is the reason for the constantly growing interest in the bone grafting research topic. Global bone grafts and substitutes market was valued at over USD 2.3 billion in 2015 and is expected to reach over USD 3.6 billion, growing at a compound annual growth rate of 5.2% during the forecast period of 2016 to 2024. An increasing number of surgeries performed on young people (at the age of 19-40 years old), as well as an aging society force scientists from the field of material engineering to develop new bone substitutes with superior properties, that will be able to enhance the healing process and allow for the reconstruction and regeneration of bone.

Photolithography hydrogels can be used to create in vitro 3D scaffolds that have many TE applications such as bone repair. Photolithography is a process that is commonly used in micro-fabrication to produce the desired scaffold with specific shape and size using a mold. Polyethylene glycol diacrylate (PEGDA) is an important class of photosensitive polymer with many tissue engineering applications. Despite intensive research, PEGDA scaffolds are unable to meet the functional requirements for bone repair in the musculoskeletal system. The ability to control the porosity of photosensitive hydrogel such as polyethylene Glycol Diacrylate (PEGDA) to elicit altered cell behaviors, including cell adhesion, has raised heightened interest in the scaffold materials for various biomedical applications, including orthopedic repair and regeneration. Several PEGDA hydrogel scaffolds have been developed for the in vitro tissue reconstruction, although the in vivo performances to evaluate the feasibility of using PEGDA at physiological conditions have not been reported yet.

PEGDA scaffolds having thickness higher than 1 mm have only limited applications as a three-dimensional (3D) cell culture device due to the inability of cells to survive within the scaffolds. Cells that are placed deep inside the PEGDA scaffold with a thickness higher than 1 mm die out because of not having access to adequate nutrients. Lack of porosity in the PEGDA scaffold leads the cells to non-uniform tissue regeneration. PEGDA scaffolds need to be designed with intricate architecture, porosity, pore size and shape, and interconnectivity in order to provide the required structural strength, nutrient transport, and micro-environment for cell and tissue in-growth. There is a significant need for operable methods that can overcome the limitations exhibited by thick PEGDA for TE applications. Various PEGDA-based scaffolds have been researched, however none of them fulfill all the requirements for TE applications. Overcoming the functional deficits of PEGDA for TE applications motivates the present invention.

SUMMARY OF THE INVENTION

The present invention provides a novel approach for controlled application of aligned electrospun fiber layers and photosensitive biomedical polymer to create 3D scaffold. Electrospinning is a process by which fibers with micro to nano meter diameters can be obtained from an electrostatically driven jet of polymer solution. These fibers have a high surface area to volume ratio, which can have numerous biomedical applications. Particularly, the electrospun fiber can be used to create aligned or random fiber matrix of thickness around ~20 microns for the growth of cell in vitro in two dimensions (2D). Methods and apparatus for controlling alignment and deposition of electrospun nanofiber (ENF) are disclosed in U.S. Pat. No. 9,359,694 and co-pending application Ser. No. 14/734,147 both by the present inventor, and the disclosures of which are incorporated herein by reference in their entirety.

Biomaterial scaffolds need to be designed to grow bone cells in three dimensions (3D). Scaffolds also need to be porous to give support to the growth of these cells. A major challenge of using ENF to create a 3D cell culture device is that when nanofiber layers are stacked together more than microns thick, the fiber matrix loses the porosity needed to grow cells in 3D. In addition, it is not possible with current methods to maintain alignment of fiber in the fiber matrix after depositing more than two or three layers of aligned fiber layers due to the repulsive characteristics of the fiber comprising each of the layers. The present invention (FIG. 1) solves this problem and enables development of a higher thickness ENF-based 3D scaffold for tissue engineering applications. A scaffold produced by the methods of the present invention provides better performances than currently available commercial scaffolds that are microfiber based and severely limited in thickness.

The biological functions of a PCL membrane depend on the number of fiber layers, fiber diameter, and type of material use to produce the membrane. The thickness of the PCL membrane is usually in the range of microns. When the thickness of the PCL membrane is larger than microns, the biological functions of the membrane decreases significantly due to the loss of porosity. The loss of porosity is higher when fibers are randomly distributed in membranes compared to membranes where fibers are aligned as in the present invention. The PCL membranes currently available in the market exhibit randomly distributed fibers and therefore have limited applications in producing scaffolds that require more than a few millimeters in thickness for tissue engineering applications.

The present invention provides a new fabrication technique to produce a 3D scaffold using polycaprolactone (PCL) electrospun nanofiber (ENF) and PEGDA membranes. The present invention enables fabrication of a PCL-ENF-PEGDA composite scaffold with appropriate thickness that dominates the disadvantages of conventional PEGDA scaffold in tissue engineering applications.

A unique feature of the scaffold enabled by the present invention is that any custom size and shape of tissue engineering graft (such as ear, nose, lips, skin) can be produced from the method provided by the present invention. The present invention provides a new 3D scaffold fabrication technique based on ENF fiber-mesh and photosensitive biomedical polymer that can be used not only for in vitro 3D cell culture medium, but can be extended to general artificial graft for damaged soft and hard tissue. The scaffold provided by the present invention can also fulfill requirements for tissue substitutes, such as: biocompatibility, bioactivity, surgical handiness, controlled resorption and biodegradation, good mechanical strength, profitable/superior microstructure after setting and hardening, appropriate working period, superior initial and final setting time, antibacterial character, relatively low price.

In one aspect, the process of the present invention enables fabrication of multiple layers of fiber-polymer matrix. The methods provided by the process enable cross aligned fiber layers to hold the polymer liquid in place and then using UV light to cure the liquid on top of each fiber layer.

In another aspect, the process of the present invention provides a method to create a composite scaffold where multiple layers of polycaprolactone (PCL) electrospun nanofiber (ENF) can be harvested to prepare PCL ENF membrane and then each membrane sandwiched between adjacent layers of PEGDA. A circular 3D PCL-ENF-PEGDA scaffold as well as other geometric and linear shapes can be constructed using the method of the present invention.

In another aspect, a single layer of aligned unidirectional PCL membrane can be intercepted on a substrate positioned between two parallel collectors. These fibers, when harvested at different angles and stacked in layers, produce an ENF membrane on the substrate.

In another aspect, the present invention provides a method enabling combined use of polycaprolactone (PCL) electrospun nanofiber ENF matrix and polyethylene glycol diacrylate (PEGDA) hydrogel to produce 3D tissue engineered structure through controlled deposition of both the hydrogel and the ENF comprising the fiber matrix.

In another aspect, PEGDA, which are hydrophilic polymer networks that absorb water, may be used to produce membranes that can be stacked and interspersed between multiple layers of PCL membranes, binding them together to produce a three dimensional (3D) composite scaffold.

In another aspect, the methods of the present invention enable fabrication of a composite PCL-ENF-PEGDA scaffold that overcomes the poor water absorption properties of a PCL membrane by combining PCL membrane with hydrogel to improve the PCL water absorption properties and promote an environment conducive for tissue growth to flourish in the scaffold.

In another aspect, the methods of provided by the process of the present invention enable fabrication of a composite PCL-ENF-PEGDA scaffold that overcomes the limitations of thick hydrogel scaffolds that have limited physical (porosity, hydrophobicity), mechanical (stiffness, elasticity) and biological (cell growth and differentiation of cells) properties.

In another aspect, the methods of provided by the process of the present invention enable fabrication of a composite PCL-ENF-PEGDA scaffold that overcomes both the individual limitations of ENF membrane and hydrogel scaffold to produce a functional bone graft.

In another aspect, the process of the present invention provides a method to create 3D scaffolds using nano-scale fibers, depositing and aligning a plurality of electrospun fiber layers on a substrate, and applying a photosensitive biomedical polymer liquid to each fiber layer deposited on said substrate.

In another aspect, deposition and cross-alignment of a plurality of electrospun fiber layers on the substrate retains polymer liquid in place before curing the polymer liquid on top of each fiber layer using UV light.

In one aspect, the present invention provides a method for fabrication of a PCL electrospun nanofiber-PEGDA 3D scaffold that includes depositing cross-aligned fibers on a substrate to produce a fiber matrix that exhibits a fiber-separation gap sufficient to prevent PEGDA gel from passing between the fibers in the fiber matrix.

In another aspect, thickness of a PEGDA gel layer on the fiber matrix is adjusted so that the PEGDA gel layer has uniform porosity.

In another aspect, the PEGDA gel layer is cured using ultraviolet light (UV) with UV curing time set to control and assure substantially uniform stiffness of the PEGDA gel layer.

In another aspect, the steps in the layering are repeated to produce a plurality of fiber matrix and PEGDA layers, and the number of layers in the plurality of fiber matrix and PEGDA layers is increased to produce a specific thickness of the 3D scaffold.

In one aspect, the present invention provides a method for producing cell-encapsulated hydrogels exhibiting complex three-dimensional (3D) structures using a PCL-ENF-PEGDA scaffold, including creating a porous fiber membrane consisting of cross-directional fibers each of the fibers being separated from another by a gap distance, and controlling porosity of the membrane by increasing or decreasing the number of cross-direction fibers to adjust the average gap distance between adjacent fibers, and flowing biological cells in a medium through the PCL-ENF-PEGDA scaffold.

In another aspect, variable porosity of the PCL-ENF-PEGDA scaffold is controlled by varying the number layers of PEGDA and varying its porosity by mixing PEGDA with osteo-conductive nanoparticles (e.g. chitin, chitosan, Hydroxyapatite).

In another aspect, porosity of the PCL-ENF-PEGDA scaffold may be adjusted by varying the number layers of PCL and varying its porosity by changing the architecture of fibers (material, diameter, distribution, number of layers) to produce the membrane.

In another aspect, the method includes infusing nutrients into the PCL-ENF-PEGDA scaffold by mixing bone growth protein (collagen, fibronectin) with PCL fiber matrix before the construction of the PCL-ENF-PEGDA scaffold using the PCL fiber matrix.

In another aspect, the method includes mixing bone growth minerals (e.g., hydroxyapatite, MgO, CaO) with the PCL fiber matrix before the construction of the PCL-ENF-PEGDA scaffold using the PCL fiber matrix.

In another aspect, the method includes mixing antibacterial agent (ZnO, silver) with the PCL fiber matrix before construction of PCL-ENF-PEGDA scaffold using the PCL fiber matrix.

In another aspect, the method includes fabricating the PCL-ENF-PEGDA scaffold using PCL membranes exhibiting a specific porosity intended to encapsulate biological cells of a specific size.

In another aspect, the method includes flowing biological cells with medium through the PCL-ENF-PEGDA scaffold multiple times.

In another aspect, various biological cell types are encapsulated using PCL-ENF-PEGDA scaffold comprising PCL membranes in PCL-ENF-PEGDA adapted with differing porosity to encapsulate a specific size of cell.

In another aspect, biological cell types may comprise at least any of cartilage cells, skin cells, organ cells, and plant cells.

BRIEF DESCRIPTION OF THE DRAWINGS

FIG. 9 depicts a table listing test results that show higher stiffness and elasticity of PCL-ENF-PEGDA composite scaffold compared to PEGDA scaffold.

DETAILED DESCRIPTION OF PREFERRED EMBODIMENTS OF THE INVENTION

Figure 1:
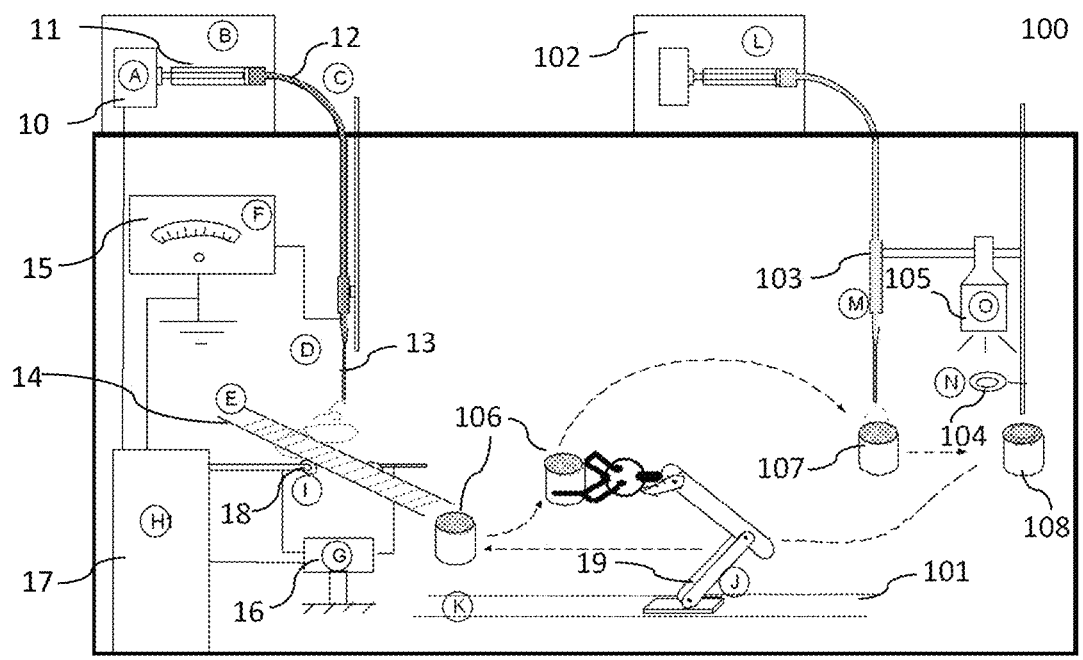
FIG. 1 is a non-limiting diagram showing a combined electrospin-UV photopolymerization unit with a robotic mechanism for automatic production of 3D scaffold of the present invention.

In brief:

FIG. 1 is a non-limiting diagram showing a combined electrospin-UV photopolymerization unit for automatic production of 3D scaffold of the present invention. The systems (electrospin and UV polymerization systems) used to produce 3D scaffold can be combined as shown. Using the automatic system as shown any number of Polyethylene Glycol Diacrylate (PEGDA) layer and PCL matrix layers can be used to produce any shape of 3D scaffold. Such scaffold can be used as an engineering scaffold for grafting of natural tissue such as liver, skin, bone etc.

Figure 2:
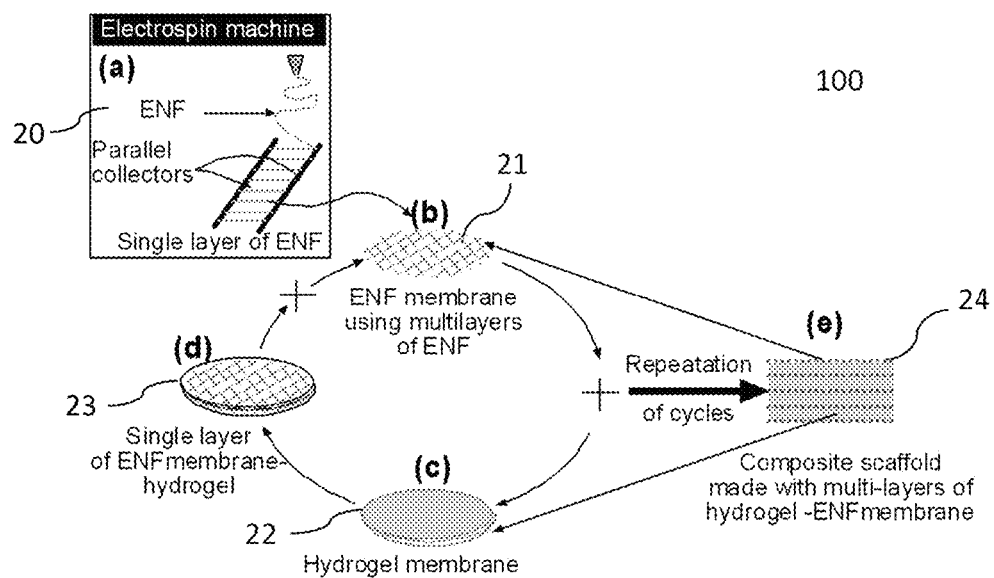
FIG. 2 is a non-limiting diagram showing a schematic view of the method of the present invention.

FIG. 2 is a non-limiting diagram showing a schematic view of the method of the present invention. The invention uses a novel approach of controlled application of aligned electrospun fiber layer and photosensitive biomedical polymer to create 3D scaffolds. The process of creating 3 layers of fiber-polymer matrix is schematically represented. The number of cross aligned fiber layers holds the polymer liquid in place and then UV light is used to cure the liquid on top of fiber layer. Using this method, at least a circular 3D scaffold can be produced.

Figure 3A:
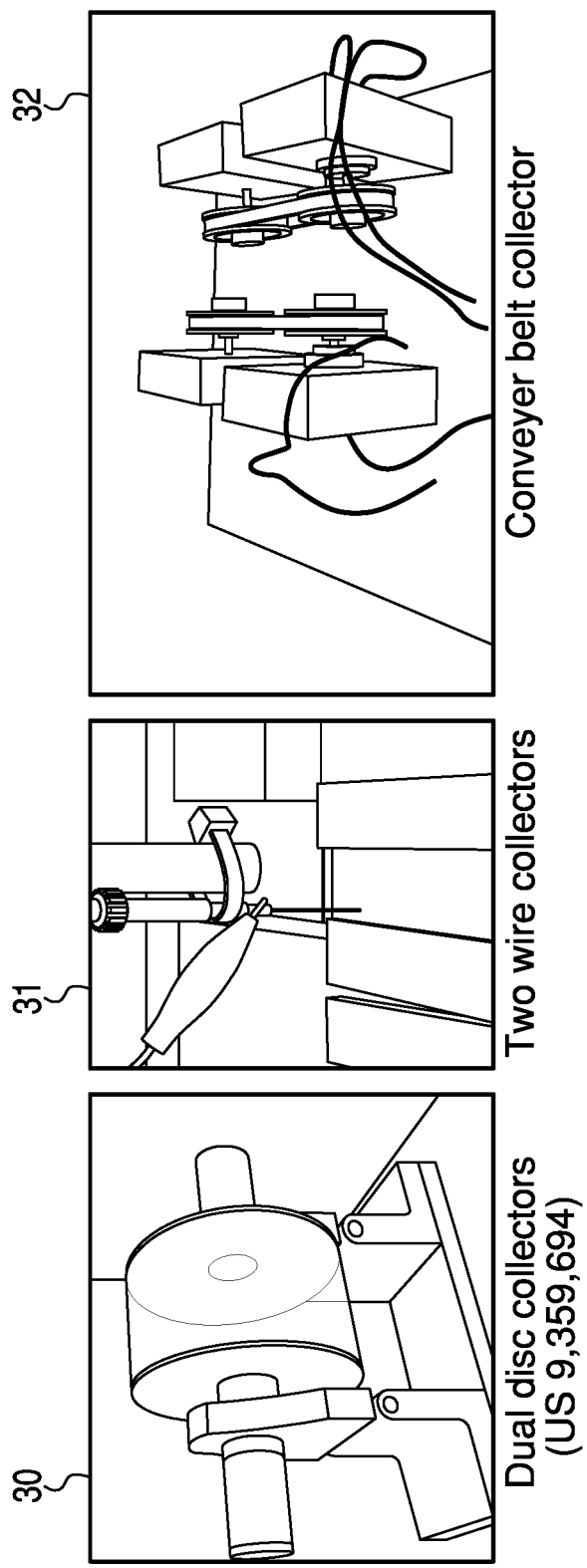
FIG. 3A is a non-limiting diagram showing equipments and accessories that may be used for fiber capture using the methods of the present invention.

FIG. 3A is a non-limiting diagram showing equipments and accessories that may be used for fiber capture using the methods of the present invention. Using an electrospin setup, parallel fibers are collected between any two parallel collectors. The collectors can be dual disc (left) or two fixed parallel wires (middle) or two parallel conveyer belt (right).

Figure 3B:
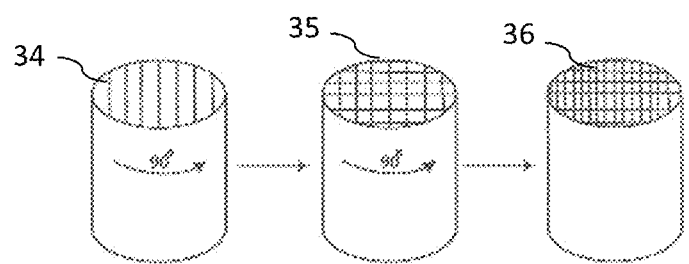
FIG. 3B is a non-limiting diagram illustrating fiber matrix layered on a substrate used for fabrication of the 3D scaffold using the method of the present invention.

FIG. 3B is a non-limiting diagram showing a substrate mold used to collect multiple layers of fiber. A mold may be used to touch the aligned fiber stream, then lowered and rotated 90° and the touch process repeated to collect another layer. The layers are coated with hydrogel where the hydrogel is held in place by the fibers. After fabrication of the two layers is complete, the mold with the fiber layers and hydrogel is positioned into a UV curing station to cure the 3D scaffold.

Figure 3C:
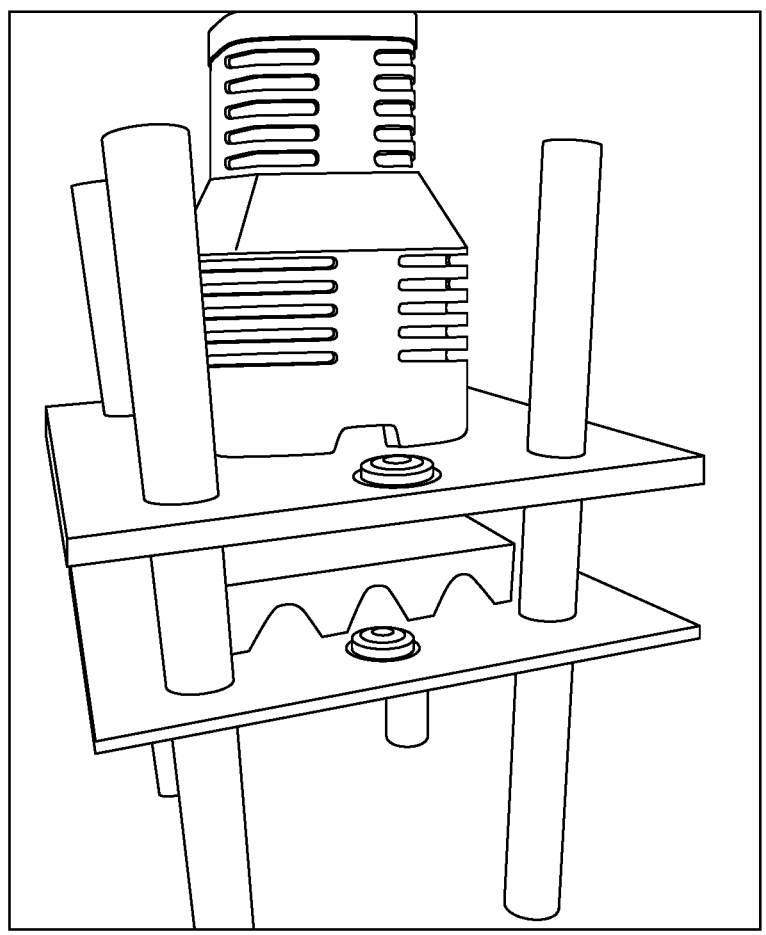
FIG. 3C is a non-limiting diagram showing UV curing station equipments and accessories used for fabrication of the 3D scaffold using the method of the present invention.

FIG. 3C is a non-limiting diagram showing UV curing station equipments and accessories used for fabrication of the 3D scaffold using the method of the present invention. Currently, in the laboratory setup the UV curing station is separated from the UV station. However, such a station can be incorporated into the chamber enclosure of the electrospining device as disclosed U.S. Pat. No. 9,359,694 and co-pending application Ser. No. 14/734,147.

Figure 3D:
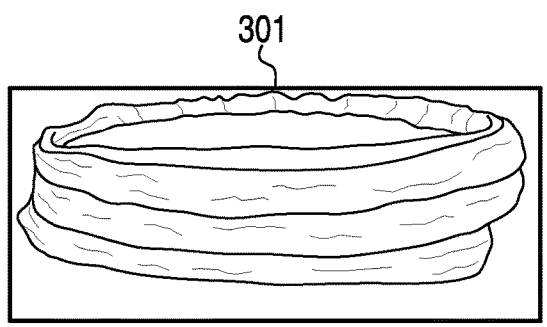
FIG. 3D is a non-limiting diagram comparing a PEGDA scaffold with a PCL-ENF-PEGDA scaffold produced using the methods of the present invention.
Figure 3D:
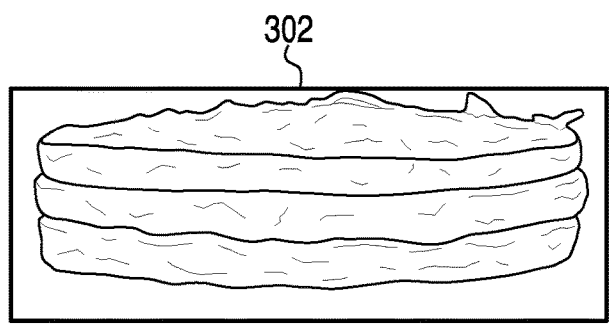

FIG. 3D is a non-limiting diagram comparing a PEGDA scaffold with a PCL-ENF-PEGDA scaffold produced using the methods of the present invention. A novel electrospun polycaprolecton (PCL) nanofiber polyethylene glycol diacrylate (PEGDA) based 3D cell culture device (9.565 mm diameter×1.5 mm thickness) was successfully prepared as shown. The scaffold was made with 3 layers of PEGDA and 4 layer PCL nanofiber matrix.

Figure 4:
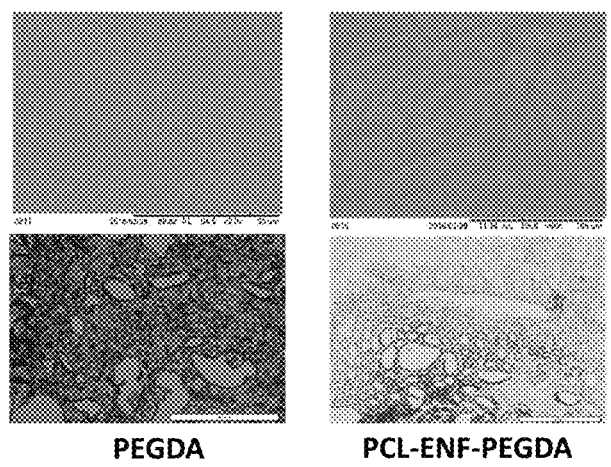
FIG. 4 is a non-limiting diagram showing SEM images of paraffin embedded and sectioned scaffolds: (a) PEGDA and (b) PCL-ENF-PEGDA.

FIG. 4 is a non-limiting diagram showing SEM images of top and longitudinally cut section views of a scaffold: (a) PEGDA and (b) PCL-ENF-PEGDA. PCL-ENF-PEGDA samples shows higher amounts of artifacts (void and presence of fibers) in comparison to PEGDA.

In detail:

Referring now to FIG. 1, a non-limiting diagram is shown illustrating a combined electrospin-UV photopolymerization unit for automatic production of 3D scaffold of the present invention. The systems (electrospin and UV polymerization systems) used to produce 3D scaffold can be combined as shown in FIG. 1. Using the automatic system as shown any number of polyethylene Glycol Diacrylate (PEGDA) layer and PCL matrix layers can be used to produce any shape of 3D scaffold. A substrate may be adapted to produce a 3D scaffold comprising at least two equal linear dimensions, or a circular shape. Such scaffold can be used as an engineering scaffold for grafting of natural tissue such as liver, skin, bone etc.

A syringe pump 10 is used to feed electrostatic polymer solution in to glass syringe 11 and flow through tube 12 to a metallic needle 13. The parallel metallic collectors 14 can be charged dual disks (30, FIG. 3A), where the disks are spun using speed controlled, direct current (DC) motors and gear mechanism. Alternatively, a pair of charged fixed wires aligned in opposing planes may be used to collect fiber (31, FIG. 3A). Another alternative is to use a conveyer system having two parallel wires that advance while collecting aligned fibers (32, FIG. 3A). The syringe needle 13 is electrically excited by applying a high-voltage in the range of (5 KVA to 15 KVA) produced by the power supply 15. This electrically charged syringe needle 13 for electrospinning synthetic polymer fiber streams is positioned above and substantially centered between the edges of parallel metallic collectors 14. This will realize an electrical potential difference between the needle tip and the collectors 14, positioning being adjustable by Z position control stage 16. As a result, electromagnetic field propagates between the charged syringe needle 13 and the edge of the collectors 14 (e.g., rotating metallic discs). This enables capturing, depositing and aligning fiber between the collectors 14. To insure a homogenous polymer injection from the needle 13, the polymer solution flow by the syringe pump 10 may be controlled by a microcontroller 17 and a rack-and-pinion gear setup in the parallel collectors 18. The microcontroller 17 may also be used to optimize the distance between the parallel collectors 14, the distance between collectors 14 and the needle 13, and the distance from the collectors 14 and a base support (not shown). An anti-vibration Z position control stage 16 may be incorporated to the base support to maximize the parallelism of the fiber lines captured by the collectors 14. A pair of gear boxes may be utilized when the collectors 14 are configured as rotating disks to help in changing the rotation direction between shafts to optimize the parameters.

A robotic arm mechanism 19 operating on a track 101 may be used to collect fiber from the collectors 14 to assemble layers on a substrate 106 and feed it to the curing station 105 without manually intervening in this process. In the last stage of the system 100, the robotic arm 19 may be integrated with the PEGDA developing process via interaction with the UV curing station, positioning substrate 106 in line with a spray/needle tip 103 supplied by second syringe pump 102 to deposit controlled amounts of PEGDA on the top of fiber matrix on the substrate 107. A mold or mask 104 can be used to cure any desired shape of PEGDA layer on the top of fiber matrix using a UV light 105.

Referring now to FIG. 2, a non-limiting diagram is shown schematically illustrating the method of the present invention for creating a composite scaffold made from three layers of PCL-ENF-PEGDA membranes. The embodiment shown in the diagram uses a novel approach of controlled application of aligned electrospun fiber layer and photosensitive biomedical polymer to create 3D scaffolds. A single layer of aligned unidirectional PCL ENF is intercepted on a substrate positioned between two collectors in the ENF machine 20, where PCL beads may be dissolved with acetone (15 wt %) to produce the fibers. The fibers may be harvested at 90° angles and stacked in layers to produce an ENF membrane 21 on a substrate. The ENF membrane 21 may be subsequently layered with a PEGDA hydrogel 22 that is cured by exposure to UV light (FIG. 3C), thereby creating a composite PCL-ENF-PEGDA scaffold 23. FIG. 3D shows 1.5 mm thickness PEGDA hydrogel 301. Multiple layers of ENF membranes were interspersed and bonded together by 0.3 mm PEGDA layer to produce a three dimensional (3D) PCL-ENF-PEGDA composite scaffold (FIG. 3D 302) shows produced 1.5 mm thickness PCL-ENF-PEGDA scaffold.

The fabrication of a PCL electrospun nanofiber-PEGDA 3D scaffold in the present invention requires the following unique features of the process:

1. Controlled deposition fiber collection to produce a fiber matrix having a porosity sized so that PEGDA gel does not go through the fiber matrix;
2. Thickness of PEGDA layers sized so that each layer has a substantially uniform porosity
3. UV curing time controlled to produce a substantially uniform stiffness of each PEGDA layer
4. Controlled number of fiber matrix and PEGDA layers to create a specific height scaffold.

Referring now to FIG. 3A through FIG. 3D, images are provided in FIG. 3A showing equipment and accessories used for fabrication of the 3D scaffold using the method of the present invention. The process of the present invention disclosed herein can be accomplished using a robotic arm mechanism (FIG. 1, 19). In a preliminary laboratory arrangement, such collection was made manually, for which a precise 90° rotation is almost impossible to achieve. To automate this step, a robotic arm (FIG. 1, 19) can be used to position a substrate (FIG. 1, 106) FIG. 3B 34 to collect the fiber layer from the collectors (FIG. 1, 14) FIG. 3A 30 or 31 or 32 and feed it to the curing station FIG. 3C without manually interfering in this step. Required numbers of layers of aligned fibers can be collected on a grounded custom made silicon mold chamber (FIG. 1, 106) FIG. 3B 34. After fabrication of the layers is complete, the mold chamber (FIG. 1, 106) FIG. 3B 35 with the fiber layers is fed into a UV curing station FIG. 3C to cure the 3D scaffold. The process is repeated to stack up layers of cross-aligned fibers on the mold chamber FIG. 3B 36. Currently, in the laboratory setup the UV curing station FIG. 3C is separated from the fiber capture components. However, such a station can be incorporated as an integrated step and located in the chamber enclosure of the electrospining device disclosed in U.S. Pat. No. 9,359,694 and co-pending application Ser. No. 14/734,147.

PEGDA is a UV cured polyethylene glycol diacrylate (PEGDA) hydrogel injected between the fiber layers to build the 3D fiber scaffold. A UV light source is exposed to the solution to completely cure of the PEGDA solution to a solidified state. The thickness of the PEGDA layer of the scaffold produced in our laboratory experiments was 0.5 mm. The forgoing PCL fiber mat and PEGDA steps were repeated 3 times to make 1.5 mm thick cylindrical 3D scaffold (FIG. 3D).

FIG. 4 is a non-limiting diagram showing SEM images of top and section views of a scaffold: (a) PEGDA and (b) PCL-ENF-PEGDA. Top surface of the produced samples was viewed without any embedding agent by SEM to get the top view of the scaffold. Each samples was paraffin embedded, then sectioned longitudinally and finally viewed in SEM images to produce the section views. PCL-ENF-PEGDA samples shows higher amounts of artifacts (void and presence of fibers) in compare to PEGDA.

Figure 5:
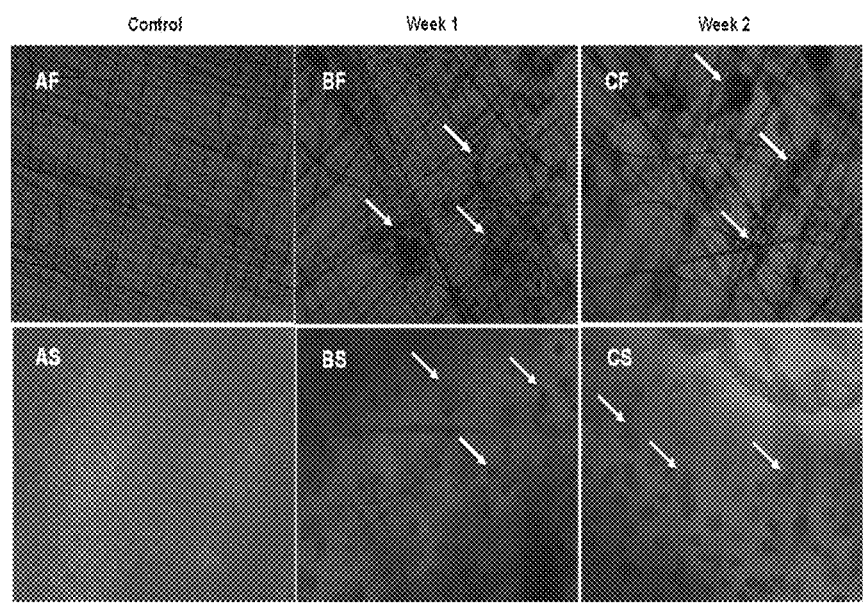
FIG. 5 is a non-limiting diagram showing human Hepatocellular carcinoma cells attached to 12 layers of PCL nanofiber (Panel BF and CF) sandwiching the PEGDA scaffold.

FIG. 5 is a non-limiting diagram showing human Hepatocellular carcinoma cells attached to 12 layers of PCL nanofiber (Panel BF and CF) sandwiching the PEGDA scaffold. Panel BS and CS represent cells growing embedded in PEGDA scaffold and clearly show that our scaffolds support cell proliferation after 2 weeks of incubation. Panel AF and AS are control PCL-ENF-PEGDA scaffold without cells. White arrows point to cells. All the scaffolds were incubated for 2 weeks. Images were taken using Olympus light microscope at 100X total magnification.

Figure 6:
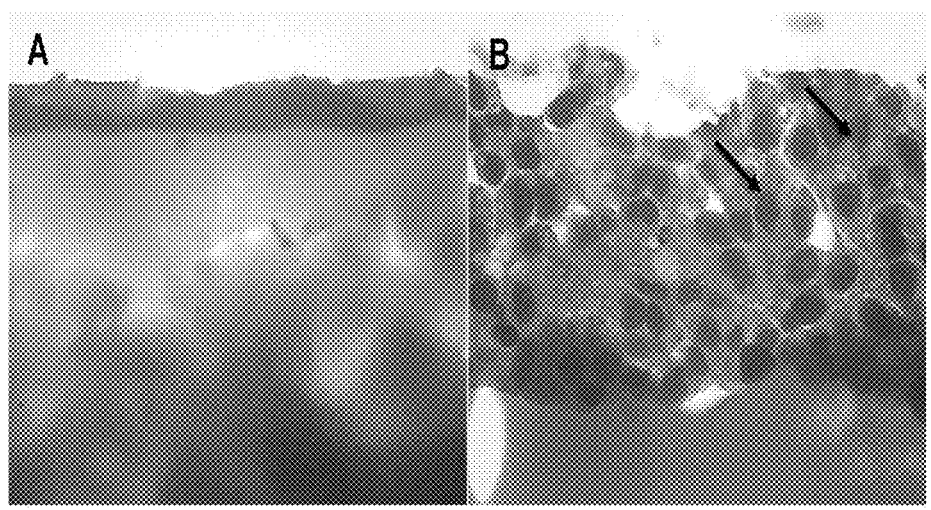
FIG. 6 is a non-limiting diagram showing H&E staining of PCL-ENF-PEGDA scaffolds with Human Hepatocellular Carcinoma cells (Panel A) 0 day and (Panel B) after 7 days of incubation.

FIG. 6 is a non-limiting diagram showing H&E staining of PCL-ENF-PEGDA scaffolds with Human Hepatocellular Carcinoma cells (Panel B) after 1 week of incubation. Black arrows in panel B point to cells. Our results clearly indicate that cells are able to migrate into PEGDA matrix. Panel A is control scaffold without any cells. Olympus light microscope at 400× magnification.

Figure 7:
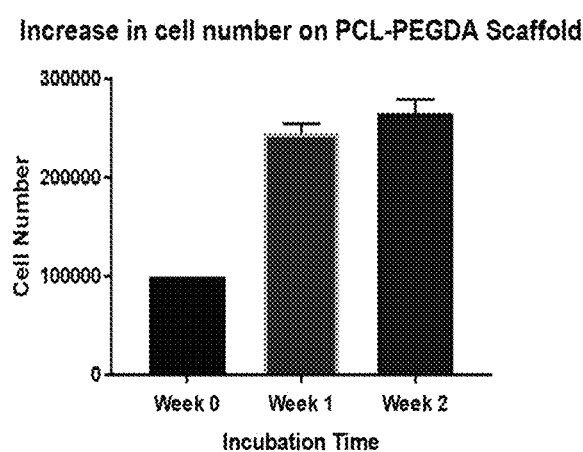
FIG. 7 is a non-limiting diagram showing human hepatocellular carcinoma cell proliferation after 14 days of culture on PCL-ENF-PEGDA scaffolds using Alamar Blue® assay.

FIG. 7 is a non-limiting diagram showing human hepatocellular carcinoma cell proliferation after 14 days of culture on PCL-ENF-PEGDA scaffolds using Alamar Blue® assay. Our results clearly indicate that cells remain viable and actively proliferating on our scaffolds. Values are mean±SD of duplicates.

Figure 8:
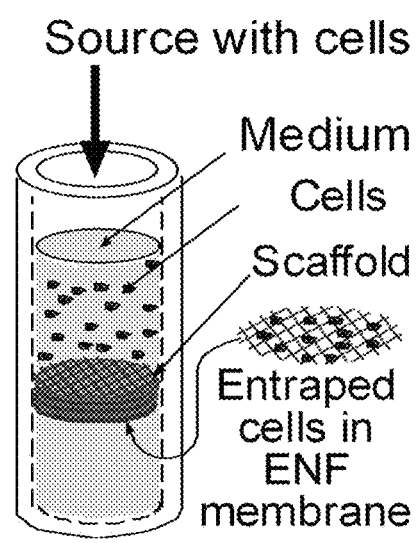
FIG. 8 is a non-limiting diagram showing the process of the cells entrapment in PCL-ENF-PEGDA scaffold.

FIG. 8 is a non-limiting diagram showing cell entrapment in PCL-ENF-PEGDA scaffold. Entrapment of cells in the scaffolds during the fabrication process is advantageous because of their homogeneous distribution. Since the porosity and entrapment of cells or nutrients are directly related, therefore, higher number of cell entrapment is possible by having higher number of fiber layers in PCL ENF membrane. Increased addition of cells in the scaffold is possible by having higher number of fiber layers in ENF membrane. This may result in an increase in cell viability, proliferation, differentiation, and spreading in vitro and in vivo compared to pristine PEGDA hydrogels and PCL-ENF-PEGDA hydrogel made with less number of fibers. Such entrapment enables excellent spatial control that can potentially be used to recapitulate the complex 3D hierarchy of the tissue microenvironment. This may have significant impact on driving the development of in vitro 3D models toward broader applications, including those in tissue engineering, cell mechanics, and bio-hybrid artificial devices and machines. Applications may include growth or fabrication of biological material derived from all biological cell types including at least any of cartilage cells, skin cells, organ cells, and plant cells.

TABLE 1 in FIG. 9 is a non-limiting diagram comparing compression and viscoelastic properties between PEGDA and PCL-ENF-PEGDA scaffolds.

Experimental Methods

Two groups of samples were prepared for this innovation: PEGDA and PCL-ENF-PEGDA samples. Morphology, mechanical and cell viability properties were examined to compare the performances of the scaffolds in relation to the performance of functional tissue graft used for biomedical applications. Both samples have same diameters (9.56 mm). A novel electrospun polycaprolecton (PCL) nanofiber polyethylene glycol diacrylate (PEGDA) based 3D cell culture device (9.565 mm diameter×1.5 mm thickness) was successfully prepared as shown. The scaffold was made with 3 layers of PEGDA and 4 layer PCL nanofiber matrix. Lever cancerous cell were cultured in the 3D scaffold.

Material

Two solutions were combined to make the final PEGDA hydrogel solution mix. The first solution consisted of the liquid Polyethylene Glycol Diacrylate (PEGDA), $M_n$=700 (mol), diluted with liquid Dulbecco's Phosphate Buffer Saline (PBS). The second solution consisted of a solute solid photo-initiator (PI) Alpha-alpha-dimethoxy-alpha-phenylacetophenone, $M_w$=256.35 (g/mol); Sigma-Aldrich, that was dissolved in the liquid solvent 1-vinyl-2-pyrrolidone, $M_w$=111.14 (g/mol). Two solutions were combined to make poly(ε-caprolactone) PCL fiber. PCL beads (pellet size ~3 mm, average $M_n$ 80,000) and acetone (laboratory reagent ≥99.5%) were mixed to prepare the PCL solution.

Specimen Preparation

PEGDA Samples:

The 20% PEGDA solution was produced by mixing 2 ml of PEGDA with 8 ml of DPBS. The PI solution was produced by mixing 0.3 (g) of PI powdered solid in 1 ml of the liquid vinyl solvent in a dark room to prevent premature cross-linked curing from light. The 0.2% PI volume concentration hydrogel solutions was produced by adding 4 μl of PI solution with 2 ml of PEGDA solution, respectively. The desired hydrogel mixtures were added to the cell pellet and vortexed to ensure thorough mixing. For curing, a 365 nanometer (nm) UV lamp was used to photo-polymerize. The UV-lamp was mounted in the electrospin chamber. The lamp was turned on 20 minutes before hydrogel curing to reach maximum UV light intensity. PEGDA was poured in to 10 mm diameter×1.5 mm thickness silicone mold and cured simultaneously in a dark room to prepare the PEGDA samples.

PCL-ENF-PEGDA Samples:

PCL solution was prepared by ultrasonic (Sonics & Materials, Inc., model # Vibra-cell VCX 130) mixing of 7.69 wt % of PCL pellets (pellet size~3 mm, average $M_n$ 80,000) with acetone (laboratory reagent ≥99.5%). The sonication process was carried out at approximately 60° C. for an 30 minutes. The solution was poured into a glass syringe in an infusion pump (Harvard Apparatus, mode # PHD ULTRA) for fiber production. PCL fibers were ejected from the glass syringe via charged needle (23G blunt needle, aluminum hub, 1" length, model # BX 25). The needle was charged by high voltage power source (Gamma High Voltage Research, Inc., model # ES 30 series).

The PCL fibers were harvested manually at approximately 90° angles and stacked in layers to produce an ENF membrane on the substrate. The PCL membranes were subsequently layered with PEGDA membranes cured by exposure to UV light, thereby creating a PCL-ENF-PEGDA scaffold. The process was repeated 3 times and finally coated by PCL membrane to create the PCL-ENF-PEGDA scaffolds Morphological Difference Between PEGDA and PCL-ENF-PEGDA:

There is clear topographical difference observed between PCL and PCL-ENF-PEGDA samples (FIG. 4). PCL-ENF-PEGDA has more porosity in compare to PCL due to the present of PCL fibers. The existence of fibers was also visible.

Mechanical Tests on PEGDA and PCL-ENF-PEGDA Samples:

They were mounted between the holders in Evex mechanical test equipment. The samples were loaded up to 35 N. The load and the corresponding displacement of the scaffolds were directly recorded from Evex machine software. The slopes of the curves were used to compare the difference of stiffness between the samples. The test results (TABLE 1) showed that the higher surface artifacts of PCL-ENF-PEGDA composite scaffold compared to PEGDA scaffold. The average stiffness of PCL-ENF-PEGDA composite scaffold (5.36 N/mm) is approximately 2 times higher than that of PEGDA scaffold (3.00 N/mm). The results indicated that PCL-ENF-PEGDA composite scaffold strength was higher compared to PEGDA. The results confirm that PCL ENF membrane can reinforce the PEGDA scaffold. Further improvement of stiffness and other mechanical properties of PEGDA scaffold is possible by controlled deposition of PCL ENF membrane in the scaffold. Results showed that our developed scaffolds satisfied the minimum compressive modulus requirement for bone graft substitutes (>0.5 MPa). We have conducted cell viability studies on the scaffold to evaluate and confirm its biological compatibility.

Cell Viability on PCL-ENF-PEGDA Samples:

Biocompatibility of PCL-ENF-PEGDA composite scaffolds using human hepatoma cells at different time interval. The composite scaffold also facilitated the slow diffusion of oxygen and nutrients necessary for cell proliferation and differentiation (FIGS. 6A and 6B) The results show that PCL-PEGDA scaffold promotes highly desired cell arrangement with more hepatoma cells attachment at fiber junctions compared to PE (FIG. 6B). There is in increased number of cell growth in the PCL-ENF-PEGDA scaffold was observed with time (FIG. 7). These results prove that PEGDA-PCL scaffold promotes cell viability and proliferation.

The invention claimed is:

1. A process for producing cell-encapsulated hydrogels exhibiting complex three-dimensional (3D) structures consisting of:
creating a porous fiber membrane sequencing cross-directional electrospun PCL nanofibers and PEGDA hydrogel in alternating layers;
controlling porosity of said porous fiber membrane by completing steps selected from the group consisting of increasing or decreasing the number of said nanofibers in a layer, varying the number of PCL nanofiber layers and PEGDA hydrogel layers, mixing PEGDA hydrogel with osteo-conductive nanoparticles including any of chitin, chitosan, and hydroxyapatite, and changing the architecture of said PCL nanofibers by altering any of fiber material, diameter, and distribution;
flowing biological cells at least once in a medium through said porous fiber membrane, said biological cell types being selected from a group consisting of cartilage cells, bone cells, skin cells, organ cells, and plant cells,
wherein said porous fiber membrane is created by completing at least the steps of depositing and aligning a plurality of electrospun PCL nanofiber in a first layer of PCL nanofibers, depositing on to said first layer of PCL nanofibers a plurality of electrospun PCL nanofiber in a second layer of PCL nanofibers, said plurality of PCL nanofibers in said second layer being cross-aligned relative to said plurality of PCL nanofibers in said first layer to present a first PCL-ENF matrix, applying photosensitive PEGDA hydrogel as a coating on to and substantially covering said first PCL-ENF matrix to create a first PEGDA hydrogel layer, and curing said first PEGDA hydrogel layer using ultra violet (UV) light to achieve a desired stiffness, constructing a second PCL-ENF matrix applied to said first PEGDA hydrogel layer, coating said second PCL-ENF matrix with photosensitive PEGDA hydrogel to create a second PEGDA hydrogel layer, and curing said second PEGDA hydrogel layer to achieve a desired stiffness, constructing a third PCL-ENF matrix applied to said second PEGDA layer; and
wherein said cell-encapsulated hydrogels exhibiting complex three-dimensional (3D) structures are fabricated in any custom size and shape of tissue engineering scaffold selected from the group consisting of ear, nose, lip, skin, organ, bone, and cartilage.

* * * * *

UNITED STATES PATENT AND TRADEMARK OFFICE
CERTIFICATE OF CORRECTION

| | | |
|---|---|---|
| PATENT NO. | : 10,953,133 B2 | Page 1 of 1 |
| APPLICATION NO. | : 15/439650 | |
| DATED | : March 23, 2021 | |
| INVENTOR(S) | : Morshed Khandaker and Shahram Riahinezhad | |

It is certified that error appears in the above-identified patent and that said Letters Patent is hereby corrected as shown below:

In the Specification

At Column 1, please delete Lines 19-22 and insert in its place the following:
-- This invention was made with government support under GM103447 awarded by the National Institutes of Health. The government has certain rights in the invention. --

Signed and Sealed this
First Day of November, 2022

Katherine Kelly Vidal
*Director of the United States Patent and Trademark Office*